United States Patent [19]

Brittain et al.

[11] Patent Number: 5,185,452
[45] Date of Patent: Feb. 9, 1993

[54] BENZHETEROCYCLYL SULPHONES

[75] Inventors: David R. Brittain, Rochdale; Michael T. Cox, Congleton, both of England

[73] Assignee: Imperial Chemical Industries PLC, London, England

[21] Appl. No.: 474,940

[22] Filed: Feb. 5, 1990

[30] Foreign Application Priority Data

Feb. 3, 1989 [GB] United Kingdom ................ 8902407
Feb. 3, 1989 [GB] United Kingdom ................ 8902410

[51] Int. Cl.$^5$ .......................................... C07D 209/42
[52] U.S. Cl. .................................. 548/492; 548/462; 549/269; 549/283; 549/355; 549/398; 549/462; 540/593; 540/523; 546/152; 546/156
[58] Field of Search ................ 548/491, 462; 549/401, 549/269, 283, 303, 355, 308, 420, 462, 12, 28, 57, 70; 540/593, 523; 568/929, 80, 34, 74, 75, 76, 77; 546/152, 186, 164, 180, 346; 574/213, 311, 312, 415, 418, 431, 434, 443, 445, 459, 460, 420, 886

[56] References Cited

U.S. PATENT DOCUMENTS

| | | | |
|---|---|---|---|
| 3,882,247 | 5/1975 | Bullock | 514/709 |
| 4,053,633 | 10/1977 | Goralski | 424/337 |
| 4,309,554 | 1/1982 | Goralski | 549/62 |
| 4,567,004 | 1/1986 | Blank et al. | 568/30 |
| 4,670,470 | 6/1987 | Firestone | 514/665 |
| 4,831,045 | 5/1989 | Tanouchi et al. | 514/369 |

FOREIGN PATENT DOCUMENTS

| | | | |
|---|---|---|---|
| 0304190 | 2/1989 | European Pat. Off. | |
| 0340010 | 2/1989 | European Pat. Off. | 548/491 |
| 1229653 | 4/1971 | United Kingdom . | |

OTHER PUBLICATIONS

STN Print Out, 9th Collective Index, Aug. 1978.
J. Chem. Soc., Chemical Communications, 1984, 670.
J. Organic Chemistry, 1978, 43, 3101.
J. Chem. Soc., Chemical Communications, 1978, 362.
J. Organic Chemistry, 1986, 51, 1012–1015.
Chemistry Abstracts, vol. 104, Abstract No. 168055.
J. Prakt. Chem., 1920, 101, 136–137.
Chemical Abstracts vol. 15, pp. 1013–1014.
Rec. Trav. Chim. Pays Bas, 1974, 93, 11–14.
Chemical Abstracts, vol. 59, Abstract No. 634.
J. Polymer Science, Polymer Chemistry Edition, 1985, 23, 1963–1972.
J. Heterocyclic Chemistry, 1977, 14, 1415–1416.

Primary Examiner—José Dees
Assistant Examiner—Deborah D. Carr
Attorney, Agent, or Firm—Cushman, Darby & Cushman

[57] ABSTRACT

The invention concerns novel, pharmaceutically useful, benzheterocyclyl sulphones of the formula I:

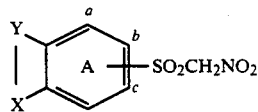

in which ring A may bear optional halogeno, (1–4C)alkyl or fluoro(1–4C)alkyl substituents; X is oxygen, or a group of the formula —S(O)$_n$— or —NR$^1$— in which n is zero, 1 or 2 and R$^1$ is hydrogen, (1–4C)alkyl, (1–6C)alkanoyl, benzoyl or phenyl(1–4C)alkyl, the last two optionally substituted; Y is various linking groups defined hereinafter, such as ethylene or trimethylene; and in which the group —SO$_2$CH$_2$NO$_2$ is located at position a, b or c in ring A; together with the non-toxic thereof. Other aspects of the invention include the production of the novel compounds by analogy processes and pharmaceutical compositions of the novel compounds for use in the treatment of diabetic complications.

6 Claims, No Drawings

BENZHETEROCYCLYL SULPHONES

TECHNICAL FIELD

This invention concerns novel benzheterocyclyl sulphone derivatives which are inhibitors of the enzyme aldose reductase and which are of value, for example, in the treatment of certain peripheral effects of diabetes or galactosemia. A method of treating one or more of such peripheral effects using a benzheterocyclyl sulphone derivative and pharmaceutical compositions containing such a derivative are also provided. In addition, the invention concerns novel processes for the manufacture of the novel derivatives and for the preparation of medicaments containing any of the said derivatives.

BACKGROUND TO INVENTION

The enzyme aldose reductase is responsible for the catalytic conversion of aldoses, such as glucose and galactose, to the corresponding alditols, such as sorbitol and galactitol respectively, in warm blooded animals such as man. Alditols penetrate cell membranes poorly and, once formed, tend to be removed only by further metabolism. Consequently, alditols tend to accumulate within cells where they are formed, causing a rise in internal osmotic pressure which may in turn be sufficient to destroy or impair the function of the cells themselves. In addition, raised alditol levels may result in abnormal levels of their metabolites which may themselves impair or damage cellular function. The enzyme aldose reductase has a relatively low substrate affinity and is generally only effective in the presence of relatively large concentrations of aldose. Such large concentrations are present in the clinical conditions of diabetes (excessive glucose) and galactosemia (excessive galactose). Consequently, aldose reductase inhibitors are useful in the reduction or prevention of the development of those peripheral effects of diabetes or galactosemia which may be due in part to the accumulation of sorbitol or galactitol, respectively, in tissues such as the eye, nerve and kidney. Such peripheral effects include, for example, macular oedema, cataract, retinopathy, neuropathy and impaired neural conduction. Although a number of aldose reductase inhibitors have been discovered and clinically evaluated, there is a continuing need for alternative inhibitors. The present invention is based in part on this need and on our discovery of the unexpected inhibition of the enzyme aldose reductase by certain benzheterocyclyl sulphone derivatives.

DISCLOSURE OF INVENTION

According to the invention there is provided a novel benzheterocyclyl sulphone derivative of the formula I, set out hereinafter, wherein ring A may be unsubstituted or may bear one or more substituents independently selected from halogeno, (1–4C)alkyl and fluoro(-1–4C)-alkyl; X is an oxygen atom, or a group of the formula —S(O)$_n$— or —NR$^1$— in which n is zero or the integer 1 or 2 and R$^1$ is hydrogen, (1–4C)-alkyl, (1–6C)alkanoyl, benzoyl or phenyl(1–4C)alkyl, the benzene moiety of which last two groups may be unsubstituted or bear up to 3 substituents independently selected from halogeno, (1–4C)alkyl, (1–4C)alkoxy and fluoro(1–4-C)alkyl; Y is a linking group of the formula —(CH$_2$)$_m$—, —CH$_2$CH=CH—, —(CH$_2$)$_2$.CH=CH— or —CH$_2$.CH=CH.CH$_2$—, in which m is an integer from 2 to 4 and a methylene (—CH$_2$—) group may be replaced by carbonyl, and which linking group may bear up to four (1–4C)alkyl substituents, and may be attached at either end to the group X; and wherein the group —SO$_2$CH$_2$NO$_2$ is located at the position a, b or c; or a non-toxic salt thereof.

In this specification the term "alkyl" includes both straight and branched alkyl groups but references to individual alkyl groups such as "propyl" are specific for the straight chain ("normal") version only, any branched chain isomer such as "isopropyl" being referred to specifically. An analogous convention applies to other generic terms.

It is to be understood that, insofar as certain of the compounds of formula I defined above may exist in optically active or racemic forms by virtue of one or more substituents containing an asymmetric carbon atom, the invention includes any such optically active or racemic form which possesses the property of inhibiting the enzyme aldose reductase. The synthesis of optically active forms may be carried out by standard techniques of organic chemistry well known in the art, for example by synthesis from optically active starting materials or by resolution of a racemic form. Similarly, inhibitory properties against aldose reductase may be evaluated using the standard laboratory tests referred to hereinafter.

Particular values for an optional substituent on ring A include the following, by way of example:

for halogeno: fluoro, chloro, bromo and iodo;
for (1–4C)alkyl: methyl, ethyl, propyl and t-butyl; and
for fluoro(1–4C)alkyl: trifluoromethyl, pentafluoroethyl, 2,2,2-trifluoroethyl and 3,3,3-trifluoropropyl.

Particular values for the group R$^1$ when it is (1–4C)alkyl, (1–6C)alkanoyl or phenyl(1–4C)alkyl include the following, by way of example:

for (1–4C)alkyl: methyl, ethyl, propyl and butyl;
(1–6C)alkanoyl; formyl and (2–4C)alkanoyl, such as acetyl, propionyl, and butyryl; and
for phenyl(1–4C)alkyl: phenylmethyl, 1-phenylethyl, 2-phenylethyl and 3-phenylpropyl.

A particular value for an optional substituent on a phenyl moiety on R$^1$ when it is benzoyl or phenyl(1–4-C)alkyl is, for example, fluoro, chloro, bromo, methyl, ethyl, methoxy, ethoxy and trifluoromethyl.

Particular values for the linking group Y include the following, by way of example: ethylene, trimethylene, tetramethylene and the groups —CO.CH$_2$—, —CO.CH$_2$.CH$_2$—, —CH$_2$.CO.CH$_2$—, —CO.CH$_2$.CH$_2$.CH$_2$—, —CH$_2$.CH=CH— and —CO.CH=CH—, any of which linking group may optionally bear up to four (1–4C)alkyl substituents.

Particular values for a (1–4C)alkyl substituent on Y include, for example, methyl, ethyl and propyl.

Particular values for X include, for example, oxygen sulphonyl and a group of the formulae —NR$^1$—, wherein R$^1$ has the meanings defined above and is preferably hydrogen, methyl, ethyl or acetyl.

A particularly preferred value for X is for example, oxygen, imino, N-acetylimino or N-ethylamino.

Preferred values for an optional substituent on ring A include, for example, fluoro, chloro, bromo, methyl, ethyl and trifluoromethyl, of which values, methyl is particularly preferred.

A particularly preferred value for ring A is, for example, when it is unsubstituted or bears two methyl substituents.

Preferred values for linking group Y are, for example, ethylene, trimethylene, and the groups —CO.CH$_2$.CH$_2$—, —CH$_2$.CH=CH—, —CO.CH=CH— and —CH$_2$.CO—, which linking group may optionally bear up to four methyl or ethyl substituents as defined hereinbefore.

A particularly preferred value for a (1–4C)alkyl substituent on Y is, for example, methyl.

In general, it is preferred that when both ring A and linking group Y bear alkyl substituents, the combined total number of carbon atoms in said alkyl substituents is not greater than 10.

Specific preferred values for linking group Y include, for example, ethylene, trimethylene, and the groups —CH$_2$.CH$_2$.C(CH$_3$)$_2$—, —CH$_2$CH$_2$CH$_2$C(CH$_3$)$_2$—, —CO.C(CH$_3$)=C(CH$_3$)—, —CH=CH.C(CH$_3$)$_2$—, —CH$_2$.C(CH$_3$)$_2$—, —CO.CH$_2$—, —CO.C(CH$_3$)$_2$— and —CO.CH$_2$.C(CH$_3$)$_2$—.

One group of compounds of particular interest comprises indoline derivatives of the formula II wherein Z is carbonyl or a group CR$^2$R$^3$ wherein R$^2$ and R$^3$ are independently hydrogen or (1–4C)alkyl; B$^1$ and B$^2$ are hydrogen or (1–4C)alkyl; R$^1$ and ring A and the optional substituents thereon have any of the meanings defined hereinbefore; and wherein the group —SO$_2$CH$_2$NO$_2$ is located at the position a, b or c; and the non-toxic salts thereof.

A further group of compounds of particular interest comprises chroman derivatives of the formula III wherein W is methylene (—CH$_2$—) or a carbonyl group; R$^4$ and R$^5$ are independently hydrogen or (1–4C)alkyl, or R$^4$ together with R$^5$ forms a direct bond; R$^6$ and R$^7$ are independently hydrogen or (1–4C)alkyl; ring A is unsubstituted or may bear one or more substituents selected from halogeno, (1–4C)alkyl and fluoro(1–4C)alkyl; and wherein the group —SO$_2$CH$_2$NO$_2$ is located at the position a, b or C; and the non-toxic salts thereof.

A particular value for B$^1$ or B$^2$, or R$^2$–R$^7$, when it is (1–4C)-alkyl is, for example, methyl or ethyl, of which methyl is preferred.

A preferred position for the location of the —SO$_2$CH$_2$NO$_2$ group is at position b and c in any of the above compounds of the formula I, II or III, and position b is particularly preferred.

Particular novel compounds of the invention are described in the accompanying examples and are provided, together with their non-toxic salts, as a further feature of the invention. Compounds of particular interest include, for example, the compounds of formula I described in Examples 8 and 16 hereinafter, which compounds are provided together with their non-toxic salts as a further feature of the invention.

The invention further comprises pharmaceutical compositions comprising a compound of the formula I or a non-toxic salt thereof, defined above, together with a pharmaceutically acceptable diluent or carrier. The compositions of the invention may be in various conventional forms. Thus, they may be in a form suitable for oral use (for example as tablets, lozenges, hard or soft capsules, aqueous or oily suspensions, emulsions, dispersible powders or granules, syrups or elixirs), for topical use (for example as creams, ointments, gels or aqueous or oily solutions or suspensions) or for parenteral administration (for example as a sterile aqueous or oily solution for intravenous, subcutaneous, intramuscular or intravascular dosing) or as a suppository for rectal dosing.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as arachis oil, liquid paraffin or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharin or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, or esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art. Topical formulations for administration to the eye will generally be in the form of an ointment, gel or sterile solution buffered at an ophthalmically acceptable pH, for example in the range pH 7.0–7.6.

The amount of active ingredient that is combined with one or more excipients to produce a single dosage form will necessarily vary depending upon the host treated and the particular route of administration. For example, a formulation intended for oral administration to humans will generally contain for example from 0.5 mg to 1 g of active agent compounded with an appropriate and convenient amount of excipients which may vary from about 5 to about 98 percent by weight of the total composition. Dosage unit forms will generally contain about 1 mg to about 500 mg of an active ingredient.

Suitable non-toxic salts include, for example, pharmaceutically acceptable salts such as alkali metal (such as potassium or sodium), alkaline earth metal (such as calcium or magnesium) and ammonium salts, and salts with organic bases affording physiologically acceptable cations, such as salts with methylamine, dimethylamine, trimethylamine, piperidine and morpholine. In addition, for those active ingredients which are sufficiently basic, suitable non-toxic salts include, for example, pharmaceutically and physiologically acceptable acid-addition salts such as salts with hydrogen halides, sulphuric acid, phosphoric acid, citric acid and maleic acid.

The novel compounds of the invention may be obtained by standard procedures of organic chemistry already known for the production of structurally analogous compounds, for example by one or more of the procedures reviewed in the paper by Zeilstra et alia in *Rec. Trav. Chim. Pays Bas* 1974, 93, 11–14. Such procedures are provided as a further feature of the invention and are illustrated by the following procedures in which ring A, X and Y have any of the meanings defined hereinbefore.

(a) Reacting an alkali metal sulphinate of the formula IVa wherein $M^+$ is an alkali metal cation and especially sodium or potassium, with nitromethane and iodine in the presence of an alkali metal (1–6C)alkoxide such as potassium t-butoxide or sodium methoxide. The reaction is preferably carried out in the presence of a suitable polar solvent, for example, 1,3-dimethyl-3,4,5,6-tetrahydro-2(1H)-pyrimidinone (DMPU) or dimethylformamide (which are preferred), or N-methyl-2-pyrrolidone, and at a temperature in the range, for example, −30° to 20° C. and, conveniently, at about 0° C. The nitromethane is generally present in an excess.

The alkali metal sulphinates may be obtained, for example, from the corresponding sulphinic acids of the formula IVb (R=H) by reaction with the appropriate alkali metal hydroxide or (1–6C)alkoxide such as sodium or potassium methoxide or ethoxide. The sulphinic acids may themselves be obtained from the corresponding sulphonyl chlorides of the formula IVb (R=Cl) by a conventional reduction using aqueous sodium sulphite or zinc dust and water. The sulphonyl chlorides may often be obtained from the appropriate compound of the formula XIII by direct chlorosulphonation using an excess of chlorosulphonic acid, or by sulphonation to give the sulphonic acid of the formula IVb(R=OH) which is then converted to the sulphonyl chloride, for example, by reaction with phosphorus pentachloride.

(b) Reacting a sulphone of the formula V with a (1–5C)alkyl nitrate, such as ethyl, propyl, iso-butyl or iso-amyl nitrate in the presence of a strong base.

A particularly suitable strong base is, for example, an alkali metal (1–6C)alkane such as butyllithium.

The reaction is preferably carried out in the presence of a suitable solvent or diluent, for example an ether such as tetrahydrofuran or t-butyl methyl ether, and at a temperature in the range, for example, −80° to 10° C. The necessary sulphones of the formula V may be made by standard procedures well known in the art, for example by oxidation of the corresponding methylthio compound of the formula VI using analogous conditions to those described for process (c) below.

(c) Oxidising a thioether of the formula VII.

Suitable oxidising agents include those which are well known in the art for the conversion of thio to sulphonyl groups and which are compatible with the group Y and the presence of other sensitive functional groups which may be present as substituents on group X and ring A. Thus, for example, hydrogen peroxide, an organic peracid (such as perbenzoic acid) or lead tetraacetate may be used. Alternatively an alkali metal periodate (such as sodium metaperiodate), persulphate (such as potassium monopersulphate) or permanganate (such as potassium permanganate), or gaseous oxygen in the presence of a suitable catalyst such as platinum, may be employed. The oxidation is preferably carried out in a suitable conventional solvent or diluent for such oxidations, for example in acetic or propionic acid, and at a temperature in the general range, for example 0° to 80° C.

In certain cases, the corresponding sulphoxide derivative of the thioether of formula VII may be formed as an isolable intermediate. The process of the invention also includes the oxidation of such a sulphoxide intermediate to a sulphone of formula I, for example, by reaction with an alkali metal permanganate (such as potassium permanganate) in a suitable solvent such as aqueous acetic acid and at a temperature in the range, for example, 20° to 80° C.

The starting thioethers of formula VII may be obtained by conventional procedures of organic chemistry, for example, from a potassium or sodium salt of the corresponding thiols of the formula VIII by conversion to the corresponding thioacetic acids of the formula IX (or a (1–4C)alkyl ester thereof, such as a methyl or ethyl ester) by reaction with chloro- or bromo-acetic acid (or a (1–4C)alkyl ester thereof) in the presence of a suitable base. The acid IX (or a (1–4C)alkyl ester thereof) is then reacted with a (1–5C)alkyl nitrate and an alkali metal (1–6C)alkane, for example isopropyl nitrate and butyllithium, under similar conditions to those used for process (b) above, to give the alkali metal salt of the corresponding 2-nitroacetic acid of the formula XI (or the (1–4C)alkyl ester thereof). The acids of formula XI are unstable and readily decarboxylate. Acidification of the alkali metal salt of an acid of formula XI allows the isolation of a thioether of formula VII. An ester of an acid of formula XI may be hydrolysed, for example, using aqueous base, to the acid of formula XI and then acidified to produce a thioether of formula VII. The esters of the acids of formula XI may also conveniently be obtained by reacting the appropriate (1–4C)alkyl nitroacetate with the required sulphenyl chloride of the formula XII in the presence of a base such as potassium fluoride.

Alternatively, the thioethers of formula VII may conveniently be obtained, for example, by oxidative coupling of the corresponding thiol of formula VIII with nitromethane in the presence of an oxidising agent such as an alkali metal ferricyanide (conveniently potassium or sodium ferricyanide), as is illustrated in the accompanying Examples.

The thiols of formula VIII may themselves be obtained by conventional procedures of heterocyclic chemistry, for example as illustrated in the accompanying Examples.

It will be appreciated that in the formula I compounds of the invention, wherein X is the imino group —NH—, it may be necessary to protect the nitrogen atom in a conventional manner at some stage prior to carrying out one of the above procedures (a)–(c) and then remove the protecting group at the final stage. Thus, for example, the said nitrogen atom may be protected using, for example, an acyl (such as acetyl or benzoyl) protecting group. The appropriate protecting groups and the procedures necessary for the protection and deprotection of nitrogen atoms are well described in standard textbooks of organic chemistry. The invention includes a development of one of the processes (a), (b) or (c) for the production of a novel compound of formula I wherein X is the group NH, as defined hereinbefore, which is characterised by using a starting material of the formula IV, V or VII wherein X is a nitrogen atom protected with an appropriate protecting group and carrying out the appropriate removal of the protecting group as a final step.

Whereafter, when a compound of formula I in which $R^1$ is (1–4C)alkyl, (1–6C)alkanoyl, optionally substituted benzoyl, or optionally substituted phenyl(1–4C)alkyl is required, the corresponding compound of formula I wherein $R^1$ is hydrogen is alkylated or acylated, for example by reaction with a (1–4C)alkyl or optionally substituted phenyl(1–4C)alkyl halide (such as an alkyl iodide or bromide or a phenylalkyl chloride or bromide) or, for example, by reaction with a (1–6C)alkanoyl or optionally substituted benzoyl halide (such as an alkanoyl chloride or bromide or a benzoyl chloride or bromide). The reaction may also optionally be performed in the presence of a strong base, for example an alkali metal hydride (such as sodium hydride) or using the preformed alkali metal salt (such as the lithium, sodium or potassium salt) of the compound of formula I in which R is hydrogen and in a suitable solvent or diluent such as N,N-dimethylformamide, tetrahydrofuran or t-butyl methyl ether and at a temperature in the general range, for example, 0°–60° C.

Whereafter, when a compound in which ring A bearing a halogeno substituent is required, it may be obtained, for example, by using a direct halogenation procedure well known in the art, for example bromination in acetic acid at a temperature in the general range 0°–40° C.

Whereafter, when a compound in which X is sulphinyl or sulphonyl is required, it may be obtained, for example, by conventional oxidation of the corresponding thio compound in which X is sulphur. Such a procedure may be conveniently carried out in combination with process (c) above, for example, as described in Example 14.

In addition, it will be appreciated that when a compound of the formula I in which $R^1$ is (1–4C)alkyl or optionally substituted phenyl(1–4C)alkyl is required, the corresponding compound of the formula I wherein $R^1$ is (1–4C)alkanoyl or optionally substituted benzoyl or phenyl(2–4C)alkanoyl may be reduced using a suitable reducing agent (such as tetrabutylammonium borohydride), in a suitable solvent, such as dichloromethane, and at a temperature in the general range of 20° to 80° C.

Whereafter, when a non-toxic salt is required, a compound of formula I may be reacted with an appropriate base having a non-toxic cation, or, when the compound of the formula I is sufficiently basic by virtue of the nature of the group —$NR^1$—, a non-toxic, acid-addition salt may be prepared by reaction with an appropriate acid having a non-toxic anion.

Many of the starting materials referred to herein are novel, for example the sulphinic acids of formula IVb(R=H) and the thioethers of formula VIII and are provided as a further feature of the invention.

As stated previously, the compounds of formula I inhibit the enzyme aldose reductase. The compounds are thus of value, for example, in treating those diseases or conditions which are caused by excessive quantities of the products such as sorbitol formed in the body by processes catalysed by the enzyme aldose reductase.

The property of inhibiting the enzyme aldose reductase in vivo may be demonstrated in the following standard laboratory test:

Rats are made diabetic (as evidenced by severe glucosuria being present) by dosing with streptozotocin. The animals are then dosed daily with the test compound for one, two or five days. The animals are then sacrificed 2–6 hours after the final dose and the eye lenses and/or sciatic nerves are removed. After a standard work-up procedure the residual sorbitol levels in each tissue are determined by gas liquid chromatography after conversion to the polytrimethylsilyl derivatives. Inhibition of aldose reductase in vivo can then be assessed by comparing the residual sorbitol levels in tissues from the dosed diabetic group of rats with those of an undosed group of diabetic rats and an undosed, normal group of rats.

The property of inhibiting the enzyme aldose reductase may also be demonstrated in vitro. Thus, in a standard procedure partially purified aldose reductase is isolated in known manner from bovine lenses. The percentage inhibition of this enzyme's ability in vitro to catalyse the reduction of aldoses to polyhydric alcohols, and particularly to reduce glucose to sorbitol, caused by a test compound can then be determined using standard spectrophotometric methods.

By way of illustration of the aldose reductase inhibitory properties of compounds of formula I, the compound of Example 2 had an $IC_{50}$ of $1.3 \times 10^{-8}M$ in the above in vitro test.

In general, compounds of the formula I show significant inhibition in the above mentioned in vivo test at a dose (generally p.o.) of 100 mg/kg or much less with no evidence of overt toxicity, and have an $IC_{50}$ in the above mentioned in vitro test of $10^{-6}M$ or much less.

The compounds of formula I will primarily be administered systemically (generally by mouth) to a warm-blooded animal to produce a therapeutic or prophylactic effect mediated by inhibition of the enzyme aldose reductase, for example at a daily dose in the range of 1 to 40 mg/kg. In man it is envisaged that a total daily dose in the range 15 to 800 mg. per man will be administered, given if necessary, in divided doses. However, the precise amount of compound administered will naturally vary somewhat, for example, with the age and sex of the patient and the severity and extent of the condition being treated.

The compounds of formula I may also be administered topically, for example by topical administration direct to the tissue or organ in which inhibition of the enzyme is required, for example by topical administration to the eye. The precise amount of compound administered will necessarily depend on the formulation used. Thus, for example, when a solution is administered a concentration of the compound containing up to 0.01% by weight will generally be used. Similarly, when an ointment is administered a concentration of the compound of up to 2% by weight will generally be used. Topical formulations of compounds of formula I may be administered to the eye of an animal, for example, man or dog, requiring treatment and/or prevention of diabetic cataracts or retinopathy, in a conventional manner, for example, using a drop or eyewash topical formulation.

The compositions may also contain one or more other agents which are known to have a useful effect in the treatment of diabetes or galactosemia, for example a hypoglycaemic agent such as tolbutamide, chlorpropamide or glybenclamide.

The invention will now be illustrated by the following non-limiting Examples in which, unless otherwise stated:

(i) Solvents were removed by rotary evaporation in vacuo with a bath temperature of 40°-50° C.;
(ii) all operations were carried out at room temperature, that is in the range 18°-26° C.;
(iii) column and flash chromatography was carried out on silica (Merck Art. 7736) and medium pressure liquid chromatography (MPLC) on silica (Merck Art. 9385), both materials available from E Merck and Co., Darmstadt, West Germany; and preparative layer chromatography (PLC) was carried out on silica coated plates (Schleicher & Schull Art. G1505/LS254), available from Schleicher & Schull, Dassel, West Germany;
(iv) the purity of chemical products was assessed by nuclear magnetic resonance (NMR) spectroscopy, thin layer chromatographic analysis, mass spectroscopy and/or microanalysis;
(v) NMR spectra were determined in deuterochloroform ($CDCl_3$) at 200 MHz and are given in delta values (parts per million) relative to tetramethylsilane as standard; conventional abbreviations for signal types are used, such as s, singlet; d, doublet; dd, doublet of doublets; br, broad; et cetera;
(vi) petroleum ether (b.p. 60°-80° C.) is referred to as "petrol 60°-80° C.";
(vii) yields are for illustration only and are not necessarily the maximum attainable by diligent process development; and
(viii) all end-products had microanalyses and NMR spectra consistent with the indicated structures.

EXAMPLE 1

Nitromethane (0.92 ml, 17 mmol) was added dropwise to a stirred solution of potassium t-butoxide (0.84 g, 8.4 mM) in N,N-dimethylformamide (DMF; 40 ml) at −5° C. When the addition was complete, stirring was continued for 30 minutes at −5° C. Sodium 2,3-dimethyl-4-oxo-4H-chromene-6-sulphonate (2.2 g, 8.5 mM) was then added, followed immediately by iodine (1.07 g, 4.2 mM). The mixture was allowed to attain ambient temperature and stirred overnight. The reaction mixture was then added to a solution of citric acid (15 g) and sodium metabisulphite (3 g) in water (150 ml). The aqueous mixture was extracted with dichloromethane ($3 \times 50$ ml) and the combined organic extracts were washed with sodium chloride solution. The solvent was removed by evaporation and the residual semi-solid purified by flash vacuum chromatography on silica, eluting with ethyl acetate/hexane (1:1 v/v), to give 2,3-dimethyl-6-(nitromethyl-sulphonyl)-4H-chromen-4-one as a solid (178 mg, 7.1% yield), m.p. 206°-209° C. [after recrystallisation from toluene]; NMR ($d_6DMSO$): 2.0(3H,s), 2.45(3H,s), 7.5(2H,s), 7.75(1H,d), 8.1(1H,dd), 8.45(1H,d); microanalysis, found: C,49.0; H,3.6; N,4.7%; $C_{12}H_{11}NO_6S$ requires: C,48.5; H,3.6; N,4.7%.

The starting material was obtained as follows:

2,3-Dimethyl-4-oxo-4H-chromene-6-sulphonyl chloride (obtained as described in J. Org. Chem., 1956, page 1104) (3.05 g, 11.2 mM) was added in small portions to a vigorously stirred solution of sodium hydrogen carbonate (1.88 g, 22.4 mM) and anhydrous sodium sulphite (2.54 g, 20.2 mM) in water (14 ml) at 75° C. When the addition was complete, the mixture was vigorously stirred at 75° C. for 45 minutes. The clear solution was allowed to cool to ambient temperature, diluted to 20 ml with water, and acidified with 2M hydrochloric acid at 0° C. The precipitated solid was collected by filtration, washed with a minimum of cold water, and air dried to give 2,3-dimethyl-4-oxo-4H-chromene-6-sulphinic acid as a white solid (2.16 g). This acid was converted to its sodium salt by addition of a methanolic solution of sodium methoxide [prepared from sodium (0.12 g) and methanol (100 ml)], and evaporation of the solution. The resultant sodium salt, obtained as a cream solid, was used immediately without further purification.

EXAMPLE 2

Using a similar procedure to that described in Example 1, there was obtained 2,2,5,7,8-pentamethyl-6-(nitromethylsulphonyl)-chroman as a solid (3.7% yield), m.p. 98°–100° C. (after recrystallisation from cyclohexane); NMR: 1.35(6H,s), 1.85(2H,t), 2.15(3H,s), 2.55(6H,s), 2.65(2H,t), 5.65(2H,s); microanalysis, found: C,55.3; H,6.4; N,4.3%; $C_{15}H_{21}NO_5S$ requires: C,55.0; H,6.5; N,4.3%.

The starting sodium sulphinate was obtained by an analogous procedure to that described for the preparation of the starting material in Example 1, but using 2,2,5,7,8-pentamethylchroman-6-sulphonyl chloride, itself obtained as described in Tet. Lett., 1987, 28, 2287).

EXAMPLE 3

Using a similar procedure to that described in Example 1, there was obtained 2,2-dimethyl-6-(nitromethylsulphonyl)chroman as a solid (6.1% yield), m.p. 85°–86.5° C. (after recrystallisation from isopropanol; NMR: 1.4(6H,s), 1.85(2H,t), 2.85(2H,t), 5.55(2H,s), 6.95(1H,m), 7.6–7.7(2H,m); microanalysis, found: C,50.8; H,5.4; N,4.7%; $C_{12}H_{15}NO_5S$ requires: C,50.5; H,5.3;N,4.9%.

The starting sodium sulphinate was obtained by an analogous procedure to that described for the preparation of the starting material in Example 1, but using 2,2-dimethylchroman-6-sulphonyl chloride, itself obtained as follows:

A solution of 2,2-dimethylchroman [obtained by an analogous procedure to that described in Chem. Ber., 1904, 37, 494, for the preparation of 2,2-dimethyl-2H-chromene, but using dihydrocoumarin as starting material in place of coumarin] (50 g, 308 mM) in dichloromethane (250 ml) was added dropwise to a solution of chlorosulphonic acid (40 ml, 602 mM) and phosphorus pentachloride (50 g, 204 mM) in dichloromethane (250 ml), cooled to 5° C. under an atmosphere of argon. The colour of the solution changed from pale yellow to orange. When the addition was complete, the mixture was slowly allowed to attain ambient temperature and stirred for 2 hours. The reaction mixture was poured onto ice-water and the organic phase was separated. The aqueous layer was extracted with dichloromethane (3×20 ml), and the combined organic extracts were washed with water and dried (MgSO4). The solvent was removed by evaporation to give 2,2-dimethylchroman-6-sulphonyl chloride as a pale purple solid (42.6 g, 53% yield), m.p. 89°–92° C. (after recrystallisation from hexane).

EXAMPLE 4

Using a similar procedure to that described in Example 1, there was obtained 1-acetyl-5-(nitromethylsulphonyl)indoline as a pale yellow solid, m.p. 210° C.; NMR (d6-DMSO): 2.2(3H,s), 3.2(2H,t), 4.2(2H,t), 6.2(2H,s), 7.7–7.9(2H,m), 8.1–8.4(1H,br); microanalysis, found: C,46.5; H,4.3; N,9.6%; $C_{11}H_{12}N_2O_5S$ requires: C,46.5; H,4.2; N,9.8%; starting from 1-acetyl-5-indolinesulphonyl chloride, itself obtained by the procedure described in Zhur. Obs. Khim. 1960, 30(4), 1218–1222.

EXAMPLE 5

Tetrabutylammonium borohydride (3.85 g, 15 mM) was added to a solution of 1-acetyl-5-(nitromethylsulphonyl)indoline (1.45 g, 5 mM) in dichloromethane (30 ml), and the mixture was stirred at reflux for 18 hours. The solvent was removed by evaporation, 2M hydrochloric acid (30 ml) was added, and the mixture was heated at reflux for 20 minutes. The solution was then poured into sufficient of an ice-cold saturated solution of sodium hydrogen carbonate to adjust the mixture to pH 6. The mixture was then extracted with dichloromethane, the combined extracts were dried (MgSO4), and the solvent was removed by evaporation. The resultant yellow oil was purified by vacuum flash chromatography on silica, eluting with dichloromethane, to give 1-ethyl-5-(nitromethylsulphony)indoline as a solid, m.p. 122° C.; NMR (d6-DMSO): 1.1(3H,t), 3.0(2H,t), 3.3(2H,m), 3.6(2H,t), 6.3(2H,s), 6.6(1H,d), 7.4(1H,d), 7.5(1H,dd); microanalysis, found: C,49.3; H,5.1; N,10.4%; $C_{11}H_{14}N_2O_4S$ requires: C,48.9; H,5.2; N,10.4%.

EXAMPLE 6

1-Acetyl-5-(nitromethylsulphonyl)indoline (5.41 g, 19 mM) was added in one portion to a boiling mixture of 2M hydrochloric acid (60 ml) and ethanol (20 ml). The mixture was heated at reflux until a clear solution formed, and then for a further 5 minutes. The hot reaction mixture was poured into ice-cold saturated sodium hydrogen carbonate solution (100 ml) and then extracted with ethyl acetate. The combined extracts were dried (MgSO4) and the solvent was removed by evaporation. The resultant yellow oil was purified by vacuum flash chromatography on silica, eluting with dichloromethane, to give 5-(nitromethylsulphonyl)indoline as a pale yellow solid, m.p. 139° C.; NMR(d6-DMSO): 3.0(2H,t), 3.6(2H,t), 6.3(2H,s), 6.5(2H,s), 6.9(1H,s), 7.4–7.5(2H,m); microanalysis, found: C,44.5; H,4.1; N,11.4%; $C_9H_{10}N_2O_4S$ requires: C,44.6; H,4.1; N,11.6%.

EXAMPLE 7

Using a similar procedure to that described in Example 1, there was obtained 3,3-dimethyl-5-(nitromethylsulphonyl)-2-oxo-2,3-dihydroindole as a white solid, m.p. 204° C. (after recrystallisation from methanol); NMR(d6-DMSO): 1.3(6H,s), 6.5(2H,s), 7.1(1H,d), 7.8(1H,dd), 7.9(1H,d), 11.0(1H,s); microanalysis, found: C,46.6; H,4.5; N,9.5; $C_{11}H_{12}N_2O_5S$ requires: C,46.5; H,4.2; N,9.8%.

The starting 3,3-dimethyl-2-oxo-2,3-dihydroindole-5-sulphonyl chloride, was obtained as a solid, m.p. 126° C. (decomp.) using a similar procedure to that described in Zhur. Obs. Khim. 1960, 30(4), 1218–1222, but using 10 equivalents of chlorosulphonic acid, starting from 3,3-dimethyl-2-oxo-2,3-dihydroindole, itself obtained as a solid m.p. 149° C. (after recrystallisation from cyclohexane) by a similar procedure to that described by A Endler and E Becker in Org. Syn., Coll. Vol. IV, 1963, page 657, but using isobutyric anhydride in place of propionic anhydride.

EXAMPLE 8

A solution of potassium peroxymonosulphate ('Oxone' trade mark; 10.5 g, 17.1 mM) in water (40 ml) was added in one portion to a vigorously stirred solution of 2,2,5,7-tetramethyl-6-(nitromethylthio)chroman (3.24 g, 11.5 mM) in methanol (100) and the reaction mixture was placed in an oil bath pre-heated to 70° C. and stirred under reflux. Solid 'Oxone' (15.75 g, 25.7 mM) was added after 5 hours and the reaction mixture was cooled after 7 hours, diluted with water (500 ml) and extracted with ethyl acetate. The combined extracts were washed with brine, the solvent removed by evaporation and the solid residue purified by flash chromatography, eluting with ethyl acetate/toluene (2:98 v/v), to give 2,2,5,7-tetramethyl-6-(nitromethylsulphonyl)chroman as a solid (1.92 g, 53% yield), m.p. 110°-111° C. [after recrystallisation from cyclohexane/toluene]; NMR: 1.3(6H,s), 1.85(2H,t), 2.54(3H,s), 2.55(3H,s), 2.65(2H,t), 5.6(2H,s), 6.65(1H,s); microanalysis, found: C,53.8; H,6.2; N,4.4%; $C_{14}H_{19}NO_5S$ requires: C,53.7; H,6.1; N,4.5%.

The starting material was obtained as follows:

(i) Copper thiocyanate (prepared as described in Chem. Ber., 67B, 944) (23.6 g, 131 mM) was added to a solution of 2,2,5,7-tetramethylchroman (prepared by the method described in J. Org. Chem., 1939, 4, 311 starting from 3,5-dimethylphenol and carrying out the reaction in formic acid) (9.95 g, 52 mM) in ethyl acetate (110 ml) and the reaction mixture was stirred at 60° C. for 90 minutes, adding a further portion of copper thiocyanate (9.4 g, 52 mM) at 60 minutes to complete the reaction. After cooling, solid was removed from the reaction mixture by filtration through diatomaceous earth. The filtrate was washed with saturated sodium bicarbonate solution and brine and then evaporated. The yellow residue was recrystallised from hexane to give 2,2,5,7-tetramethyl-6-thiocyanatochroman (A) (8.62 g, 67% yield) as a white solid, m.p. 96°-97° C.; microanalysis, found: C,67.9; H,6.8; N,5.6%; $C_{14}H_{17}NOS$ requires: C,68.0; H,6.9; N,5.7%.

(ii) Lithium aluminum hydride (2.65 g, 69.6 mM) was suspended in anhydrous ether (165 ml) under an atmosphere of argon with external cooling to 15° C. A solution of the thiocyanate (A) (8.6 g, 34.8 mM) in anhydrous ether (100 ml) was added dropwise during 30 minutes and the mixture was then heated under reflux for 30 minutes. The reaction mixture was cooled and ether (80 ml) was added. Water (80 ml) was then added cautiously dropwise followed by 2M hydrochloric acid (120 ml). The organic layer was separated and combined with a further extract. The combined organic phase was washed with saturated sodium bicarbonate solution and then with brine. Evaporation of the solvent gave 2,2,5,7-tetramethylchroman-6-thiol (B) as a clear oil which was used without further purification.

(iii) The thiol (B) was added to a solution of sodium hydroxide (2.8 g, 70 mM) in water (30 ml) and stirred vigorously for 30 minutes. Nitromethane (2.3 ml, 42.5 mM) was added, followed immediately by ether (75 ml). The reaction mixture was cooled to 15° C. in a cold water bath, then a solution of potassium ferricyanide (17.2 g, 52.3 mM) in water (43 ml) was added in a steady stream and the reaction mixture was stirred at ambient temperature overnight. The mixture was acidified with 2M hydrochloric acid and extracted with ethyl acetate. The extracts were washed with water, brine, then dried ($Na_2SO_4$) and evaporated. The residual oil was purified by flash chromatography, eluting with hexane/toluene (4:1 v/v, increasing in polarity to 2:1 v/v), to give 2,2,5,7-tetramethyl-6-(nitromethylthio)chroman (3.1 g, 32% yield) as a gum; NMR: 1.3(6H,s), 1.82(2H,t), 2.4(6H, 2d), 2.61(2H,t), 5.18(2H,s), 6.6(1H,s).

EXAMPLE 9

Using a similar procedure to that described in Example 8, but starting from 2,2,4,6-tetramethyl-5-(nitromethylthio)coumaran, there was obtained 2,2,4,6-tetramethyl-5-(nitromethylsulphonyl)coumaran, in 84% yield, m.p. 144°-146° C. [after flash chromatography using ethyl acetate/toluene (2:98 v/v) as eluant, followed by trituration with hexane]; NMR: 1.5(6H,s), 2.5(3H,s), 2.6(3H,s), 3.0(2H,s), 5.6(2H,s), 6.6(1H,s); microanalysis, found: C,52.4; H,5.6; N,4.7%; $C_{13}H_{17}NO_5S$ requires: C,52.2; H,5.7; N,4.7%.

The required thioether was obtained by an analogous procedure to that described for the starting material in Example 8, but starting from 2,2,4,6-tetramethylcoumaran, itself obtained by an analogous procedure to that described in J. Org. Chem., 1970, 35 2904, starting from 3,5-dimethylphenol.

EXAMPLE 10

Using a similar procedure to that described in Example 8, there was obtained 5,7-dimethyl-6-(nitromethylsulphonyl)chroman as a white solid (41% yield), m.p. 136.5°-138° C. (after flash chromatography using dichloromethane as eluant, followed by trituration with ether/hexane); NMR: 2.05(2H,m), 2.55(3H,s) 2.6(3H,s), 2.65(2H,t), 4.18(2H,t), 5.58(2H,), 6.65(1H,s); microanalysis, found: C,50.6; H,5.2; N,4.8%; $C_{12}H_{15}NO_5S$ requires: C,50.5; H,5.3; N,4.9%.

The required thioether was obtained by an analogous procedure to that described for the starting material in Example 8, starting from 5,7-dimethylchroman, itself obtained by an analogous procedure to that described in J. Amer. Chem. Soc., 1920, 42, 157, starting from 3,5-dimethylphenol.

EXAMPLE 11

Using a similar procedure to that described in Example 8, there was obtained 5,7,8-trimethyl-6-(nitromethylsulphonyl)chroman as a cream solid (27% yield), m.p. 104°-106° C. (after flash chromatography using dichloromethane as eluant, followed by trituration with ether/hexane); NMR: 2.05(2H,m), 2.15(3H,s) 2.5(3H,s), 2.55(3H,s), 2.68(2H,t), 4.22(2H,t), 5.62(2H,s); microanalysis, found: C,52.5; H,5.6; N,4.5%; $C_{13}H_{17}NO_5S$ requires: C,52.2; H,5.7; N,4.7%.

The required thioether was obtained by an analogous procedure to that described for the starting material in Example 8, starting from 5,7,8-trimethylchroman, itself obtained by an analogous procedure to that described in J. Amer. Chem. Soc., 1920, 42, 157, starting from 2,3,5-trimethylphenol.

EXAMPLE 12

An aqueous solution of potassium permanganate (3% w/v, 25 ml; 4.7 mM) was added dropwise to a stirred solution of 2,3,4,5-tetrahydro-2,2,6,8-tetramethyl-7-(nitromethylthio)-1-benzoxepi n (1.1 g, 3.7 mM) in acetic acid (28 ml). After 1 hour, further potassium permanganate solution (3% w/v, 20 ml) was added dropwise. After 2 hours, the reaction mixture was poured into a solution of sodium metabisulphite (10 g) in water (100 ml) and extracted with dichloromethane. The combined extracts were washed with brine, dried ($Na_2SO_4$), the solvent removed by evaporation, and the solid residue purified by flash chromatography, eluting wih dichloromethane to give 2,3,4,5-tetrahydro-2,2,6,8-tetramethyl-7-(nitromethylsulphonyl)-1-benzoxepin as a solid (360 mg, 25% yield), m.p. 100°–101° C. (after recrystallisation from cyclohexane); NMR: 1.30(6H,s), 1.68(4H,m), 2.60(3H,s), 2.62(3H,s), 2.84(2H,t), 5.60(2H,s), 6.75(1H,s); microanalysis, found: C,54.9; H,6.5; N,4.2%; $C_{15}H_{21}NO_5S$ requires: C,55.0; H,6.5; N,4.3%.

The starting material was obtained as follows:

(i) Trifluoromethanesulphonic acid (0.2 ml, 2.3 mM) in dichloromethane (0.5 ml) was added dropwise to a solution of the epsilon-lactone of 3-(2-hydroxy-4,6-dimethylbenzoyl)propionic acid, [m.p. 77° C.; prepared by the method described in Acta. Chem. Scand. 1972, 26, 2372, but starting from 3-(2-hydroxy-4,6-dimethylbenzoyl)propionic acid, itself prepared as described in Liebigs Ann. Chem. 1985, 560] in dichloromethane (1 ml) at 0° C. under argon, followed by a solution of triethylsilane (200 mg, 1.7 mM) in dichloromethane (0.5 ml). After 5 minutes, a further portion of trifluoromethanesulphonic acid (0.2 ml, 2.3 mM) in dichloromethane (0.5 ml) was added followed by triethylsilane (200 mg; 1.7 mM) in dichloromethane (0.5 ml). The reaction mixture was stirred for 2 hours at ambient temperature, then poured into saturated sodium hydrogen carbonate solution and extracted with dichloromethane. The combined extracts were washed with brine, dried ($Na_2SO_4$), and the solvent was removed by evaporation. The residual oil was purified by flash chromatography, eluting with hexane/dichloromethane (1:1 v/v increasing in polarity to 1:3 v/v), giving the epsilon-lactone of 4-(2-hydroxy-4,6-dimethylphenyl)butyric acid (C) as a colourless oil; NMR: 2.10(2H,tt), 2.29(6H,s), 2.43(2H,t), 2.79(2H,t), 6.75(1H,s), 6.86(1H,s); I.R (thin film) 1720 cm$^{-1}$.

(ii) A 3M ethereal solution of methylmagnesium iodide (8 ml, 24 mM) was added dropwise to a stirred solution of the lactone (C) (1.8 g, 9.5 mM) in ether (42 ml) at 5° C. Stirring was continued at ambient temperature for 12 hours. The mixture was then cooled to 5° C., treated with excess saturated ammonium chloride solution and extracted with ether. The combined extracts were washed with brine, dried ($Na_2SO_4$) and the solvent removed by evaporation. The residual oil was purified by flash chromatography, eluting with dichloromethane/ethyl acetate (9:1 v/v increasing in polarity to 8:2 v/v) to give 5-(2-hydroxy-4,6-dimethylphenyl)-2-methylpentan-2-ol (D) (1 g, 48% yield), m.p. 128° C. (after recrystallisation from cyclohexane); NMR (d$_6$-DMSO): 0.95(6H,s), 1.33(4H,m), 1.97(3H,s), 2.01(3H,s), 2.37(2H,t), 6.24(1H,s), 6.28(1H,s); microanalysis, found: C,75.6; H,10.2%; $C_{14}H_{22}O_2$ requires: C,75.6; H,10.0%.

(iii) A solution of the diol (D) (100 mg, 0.45 mM) and p-toluenesulphonic acid (10 mg) in benzene (20 ml) was heated for 1 hour under reflux in an apparatus for the azeotropic removal of water. The reaction solution was cooled, and washed with aqueous sodium hydroxide (2M), followed by brine. The dried ($Na_2SO_4$) solution was concentrated in vacuo. The residual oil was purified by flash chromatography, eluting with toluene/hexane (1:1 v/v), to give 2,3,4,5-tetrahydro-2,2,6,8-tetramethyl-1-benzoxepin (E) as a colourless oil (90 mg, 98% yield); NMR: 1.25(6H,s), 1.63(4H,m), 2.23(3H,s), 2.25(3H,s), 2.73(2H,m), 6.57(1H,s), 6.69(1H,s).

(iv) Lead thiocyanate (6.0 g, 18 mmol) in methyl acetate (30 ml) was treated with bromine (0.86 ml, 17 mmol) at −10° C. After 30 minutes, stirring was stopped and the thus formed solution of thiocyanogen decanted into a solution of the benzoxepin (E) (2.5 g, 12.2 mM) in methyl acetate (30 ml) at −10° C. The mixture was allowed to warm slowly to ambient temperature and stirring was continued for 16 hours. Solid material was removed by filtration through diatomaceous earth. The filtrate was then washed with saturated sodium hydrogen carbonate solution, followed by brine. The dried ($Na_2SO_4$) soution was concentrated in vacuo, the solvent removed by evaporation and the residual oil was purified by flash chromatography, eluting with toluene, to give 2,3,4,5-tetrahydro-2,2,6,8-tetramethyl-7-thiocyanato-1-benzoxepin (F) as a yellow oil (2.9 g, 91%); NMR: 1.27(6H,s), 1.64(4H,m), 2.53(3H,s), 2.58(3H,s), 2.82(2H,t), 6.76(1H,s).

(v) Using a similar procedure to that described in part (ii) of Example 8, 2,3,4,5-tetrahydro-2,2,6,8-tetramethyl-1-benzoxepin-7-thiol (G) was obtained in essentially quantitive yield; mass spectrum: m/e (chemical ionisation) 254 $(M+NH_4)^+$; starting from the thiocyanto compound (F).

(vi) Using a similar procedure to that described in part (iii) of Example 8, 2,3,4,5-tetrahydro-2,2,6,8-tetramethyl-7-(nitromethylthio)-1-benzoxepin, was obtained as a solid in 38% yield; NMR: 1.27(6H,s), 1.64(4H,m), 2.45(3H,s), 2.53(3H,s), 2.82(2H,t), 5.2(2H,s), 6.76(1H,s).

EXAMPLE 13

Using a similar procedure to that described in Example 12, 2,2,7,8-tetramethyl-6-(nitromethylsulphonyl)-chroman was obtained in 50% yield as white needles, m.p. 98.5°–99.50° C. (after vacuum flash chromatography, using dichloromethane as eluant, followed by recrystallisation from cyclohexane); NMR: 1.37(6H,s), 1.83(2H,t), 2.15(3H,s), 2.55(3H,s), 2.8(2H,t), 5.6(2H,s), 7.65(1H,s); microanalysis, found: C,53.6; H,6.2; N,4.4%; $C_{14}H_{19}NO_5S$ requires: C,53.7; H,6.1; N,4.5%.

The required thioether was obtained using an analogous procedure to that described for the preparation of the starting material in Example 8, starting from 2,2,7,8-tetramethylchroman, itself obtained by an analogous procedure to that described in J. Amer. Chem. Soc., 1920, 42 157, but starting from 2,3-dimethylphenol.

EXAMPLE 14

A 35% w/v solution of peracetic acid in acetic acid (3.2 ml) was added in a slow stream to a stirred solution of 5,7-dimethyl-6-(nitromethylthio)thiachroman (500 mg, 1.86 mM) in chloroform (25 ml). The solution was then stirred and heated at 60° C. Two further quantities of 35% w/v peracetic acid solution (3.2 ml) were added after 2 hours and 3.5 hours, respectively. After 7.5 hours, the reaction mixture was cooled and a solution of sodium metabisulphite (5 g) in water (50 ml) was added slowly with further cooling. The organic layer was separated and the aqueous layer extracted with chloroform. The combined extracts were dried ($Na_2SO_4$) and evaporated. The white solid obtained was recrystallised from toluene to give 5,7-dimethyl-6-(nitromethylsulphonyl)thiachroman-1,1-dioxide (290 mg, 47% yield), m.p. 168°–170° C.; NMR: (d$_6$-DMSO): 2.38(2H,m), 2.56(3H,s), 2.65(3H,s), 2.91(2H,t), 3.55(2H,m), 6.65(2H,s), 7.79(1H,s); microanalysis, found: C,43.3; H,4.1; N,4.1%; $C_{12}H_{15}NO_6S_2$ requires: C,43.2; H,4.5; N,4.2%.

The required thioether was obtained as follows:

(i) Phosphorus pentoxide (30 g, 210 mM) was added to methanesulphonic acid (350 g, 3.65M) and the mixture stirred until solution was attained. Solid 3-[(3,5-dimethylphenyl)thio]propionic acid (obtained by a similar procedure to that described in *Boll. Sci. Fac. Chim. Ind. Bologna*, 1966, 24, 75, but starting from 3,5-dimethylthiophenol) (16.2 g, 77 mmol) was added to this solution and the mixture stirred for 5 hours, before being added to ice/water (600 ml). The aqueous mixture was extracted with ethyl acetate. The extracts were washed with saturated sodium bicarbonate solution, then brine and evaporated. The residue was purified by distillation in a Kugelrohr apparatus to give 5,7-dimethyl-4-oxothiachroman (H) as a solid (oven distillation temperature: 150° C., at 0.01 millibar pressure) (13.46 g, 98% yield); NMR: 2.27(3H,s), 2.58(3H,s), 2.99(2H,m), 3.17(2H,m), 6.78(1H,s), 6.95(1H,s).

(ii) The ketone (H) (12.83 g, 67 mM) was dissolved in trifluoroacetic acid (25.7 ml, 333 mM) and triethylsilane (23.4 ml, 146 mM) was added. The mixture was stirred and heated at 80° C. for 8 hours, then cooled, diluted wth water (500 ml) and extracted with ether. The extracts were washed with saturated sodium bicarbonate solution, then brine and evaporated. The mobile oil obtained was purified by flash chromatography eluting with hexane/toluene (9:1 v/v), followed by distillation in a Kugelrohr apparatus to give 5,7-dimethylthiachroman (I) as a solid (oven distillation temperature: 75° C., at 0.6 millibar pressure) (11.4 g, 96% yield); NMR: 2.17(3H,s), 2.2(3H,s), 2.66(2H,t), 2.95(2H,m), 6.69(1H,s), 6.78(1H,s).

(iii) Using a similar procedure to that described in part (iv) of Example 12, but starting from 5,7-dimethylthiachroman (I), 5,7-dimethyl-6-thiocyanatothiachroman (J) was obtained as a pale yellow solid, in 64% yield; NMR (C$_6$D$_6$): 1.56(2H,m), 2.06(2H,t), 2.2(3H,s), 2.25(3H,s), 2.5(2H,m), 6.88(1H,s).

(iv) Using similar procedures to that described in parts (ii) and (iii) of Example 8, but starting from 5,7-dimethyl-6-thiocyanatothiachroman (J), 5,7-dimethyl-6-(nitromethylthio)thiachroman was obtained in 44% yield as a pale yellow gum which slowly solidified; NMR: 2.17(2H,m), 2.4(3H,s), 2.43(3H,s), 2.69(2H,t), 2.95(2H,m), 5.19(2H,s), 6.91(1H,s).

EXAMPLE 15

Using a similar procedure to that described in Example 1, there was obtained in 3% yield 2,2-dimethyl-6-(nitromethylsulphonyl)chromene as a solid, m.p. 81° C. (after recrystallisation from cyclohexane); NMR: 1.5(6H,s), 5.55(2H,s), 5.75(1H,d), 6.35(1H,s), 6.9(1H,d), 7.5(1H,d), 7.65(1H,dd); microanalysis, found: C,51.1; H,4.6; N,4.7%; C$_{12}$H$_{13}$NO$_5$S requires: C,50.9; H,4.6; N,4.9%.

The required sulphinate salt used as starting material was prepared as follows:

A 1.5M solution of butyllithium in hexane (5.2 ml) was added to a stirred solution of 2,2-dimethyl-6-bromochromene [prepared by the procedure described in *Bull. Chem. Soc. Jap.*, 1982, 55(4) 1153] (2.0 g, 8.4 mM) in sodium dried ether (24 ml). The mixture was stirred for 3 hours, then cooled to −20° C. and treated with excess gaseous sulphur dioxide, whereupon the lithium sulphinate salt immediately began to separate out as a solid. The resultant suspension was stirred rapidly for one hour and then allowed to attain ambient temperature. The solid precipitate of lithium 2,2-dimethylchromene-6-sulphinate was collected by filtration and washed with dry acetone and sodium dried ether. The lithium salt was then dissolved in water and the solution acidified to pH 1 and extracted with ethyl acetate. The combined extracts were dried (Na$_2$SO$_4$) and evaporated. The resultant 2,2-dimethylchromene-6-sulphinic acid was dissolved in methanol (10 ml) containing sodium methoxide (400 mg, 7.3 mmol). After 10 minutes, the methanol was removed in vacuo to leave a solid residue of sodium 2,2-dimethylchromene-6-sulphinate, which was dried by azeotropic distillation with toluene in vacuo and used directly in the above reaction.

EXAMPLE 16

Using a similar procedure to that described in Example 1, except that an equimolar amount of sodium methoxide was used in place of potassium t-butoxide, there was obtained in 49% yield 1-acetyl-2,4-dimethyl-5-(nitromethylsulphonyl)indoline as a solid, m.p. 157° C.; NMR(d$_6$-DMSO): 1.2(3H,d), 2.3(3H,s), 2.5(3H,s), 2.7(1H,s), 3.3(1H,d), 4.8(1H,m), 6.5(2H,s), 7.8(1H,d), 8.0(1H,m); microanalysis, found: C,49.7; H,4.8; N,9.0%; C$_{13}$H$_{16}$N$_2$SO$_5$ requires: C,50.0; H,5.2; N,8.9%; starting from the corresponding 5-indolinesulphonyl chloride. The initial starting material, 2,4-dimethylindoline, was itself obtained by a similar procedure to that described in *Syn. Comm.*, 1983, 13(6) 489–493, starting from 2,4-dimethylindole.

EXAMPLE 17

Using a similar overall procedure to that described in example 16, there was obtained in 13% yield 1-acetyl-4,6-dimethyl-5-(nitromethylsulphonyl)indoline as a solid, m.p. 204° C.; NMR(d$_6$-DMSO): 2.2(3H,s), 2.45(3H,s), 2.6(3H,s), 3.1(2H,t), 4.15(2H,t), 6.4(2H,s), 7.8–8.0(1H,br); microanalysis, found: C,49.9; H,5.2; N,8.3%; C$_{13}$H$_{16}$N$_2$SO$_5$ requires: C,50.0; H,5.2; N,8.9%; starting from the corresponding 5-indolinesulphonyl chloride, itself obtained from 1-acetyl-4,6-dimethylindoline.

EXAMPLE 18

Using a similar procedure to that described in Example 16, there was obtained in 20% yield 1-acetyl-7-(nitromethylsulphonyl)-1,2,3,4-tetrahydroquinoline as a solid, m.p. 155° C.; microanalysis, found: C,48.5; H,4.7; N,9.2%; C$_{12}$H$_{14}$N$_2$SO$_5$ requires: C,48.3; H,4.7; N,9.4%; NMR: (d$_6$-DMSO): 1.9(2H,m), 2.2(3H,s), 2.9(2H,t), 3.7(2H,t), 6.5(2H,s), 7.5(1H,dd), 8.3(1H,s).

EXAMPLES 19-23

Using a similar reduction procedure to that described in Example 5, the following compounds of formula I were obtained starting from the appropriate cyclic amide:

(Example 19): 3,3-dimethyl-5-(nitromethylsulphonyl)indoline, as an oil; NMR:1.3(3H,s), 3.4(2H,s), 5.45(2H,s), 6.5(1H,d), 7.4(1H,d), 7.5(1H,dd); m/e (M-H)$^-$ 269; obtained in 25% yield starting from 3,3-dimethyl-5-nitromethylsulphonyl-2-oxo-1,2-dihydro-3H-indole (Example 7);

(Example 20): 1-ethyl-7-(nitromethylsulphonyl)-1,2,3,4-tetrahydroquinoline as a pale yellow solid, m.p. 74° C.; microanalysis, found: C,80.8; H,5.4; N,9.7%; C$_{12}$H$_{16}$N$_2$SO$_4$ requires: C,80.7; H,5.7; N,9.8%; NMR: 1.2(3H,t), 2.0(2H,m), 2.8(2H,t), 3.4(4H,m), 5.5(2H,s), 6.9(1H,d), 7.0(1H,dd), 7.1(1H,d); obtained in 39% yield starting from 1-acetyl-7-(nitromethylsulphonyl)-1,2,3,4-tetrahydroquinoline (Example 18);

(Example 21): 1-ethyl-4,6-dimethyl-5-(nitromethylsulphonyl)indoline as a pale yellow solid, m.p. 116° C.; microanalysis, found: C,52.5; H,6.0; N,9.0%, $C_{13}H_{18}N_2SO_4$ requires: C,52.3; H,6.1; N,9.4%, NMR: 1,2(3H,d), 2.4(3H,s), 2.6(3H,s), 3.0(2H,t), 3.3(2H,q), 3.6(2H,t), 5.5(2H,s), 6.1(1H,s); obtained in 35% yield, starting from 1-acetyl-4,6-dimethyl-5-(nitromethysulphonyl)indoline (Example 17);

(Example 22): 1-ethyl-2-methyl-5-(nitromethylsulphonyl)indoline as a pale yellow solid, m.p. 92° C.; microanalysis, found: C,50.7; H,5.6; N,9.8%; $C_{12}H_{16}N_2SO_4$ requires: C,50.7; H,5.6; N,9.5%; NMR: 1.2(3H,t), 1.3(2H,d), 2.7(2H,dd), 3.3(2H,m), 4.0(1H,m), 5.5(2H,s), 6.3(1H,d), 7.4(1H,d), 7.6(1H,dd); obtained in 29% yield starting from 1-acetyl-2-methyl-5-(nitromethylsulphonyl)indoline (Example 30); and (Example 23): 1-ethyl-2,4-dimethyl-5-(nitromethylsulphonyl)indoline as a pale yellow solid, m.p. 93° C.; microanalysis, found: C,52.2; H,6.2; N,9.3%; $C_{13}H_{18}N_2SO_4$ requires: C,52.3; H,6.1; N,9.4%, NMR: (200 MHz, $CDCl_3$): 1.1(3H,t), 1.3(3H,d), 2.4(3H,s), 2.5(1H,dd), 3.2(1H,dd), 3.3(2H,q), 4.0(1H,m), 5.5(2H,s), 6.2(1H,d), 7.7(1H,d) in 19% yield, starting from 1-acetyl-2,4-dimethyl-5-(nitromethylsulphonyl)indoline (Example 16).

EXAMPLES 24-28

Using a similar procedure to that described in Example 6 the following compounds of formula I were obtained by hydrolysis of the corresponding N-acetyl derivatives:

(Example 24): 7-(nitromethylsulphonyl)-1,2,3,4-tetrahydroquinoline, as a pale yellow solid, m.p. 99° C.; microanalysis, found: C,47.1; H,4.7; N,10.5%; $C_{10}H_{12}N_2SO_4$ requires: C,46.9; H,4.7; N,10.9%; NMR: 2.0(2H,m), 2.8(2H,t), 3.4(2H,t), 4.1(1H, broad), 5.5(2H,s), 6.9(1H,d), 7.1(2H,m); obtained in 60% yield, starting from 1-acetyl-7-(nitromethyl-sulphonyl)-1,2,3,4-tetrahydroquinoline;

(Example 25): 2-methyl-5-(nitromethylsulphonyl)indoline, as a pale yellow solid, m.p. 91° C.; micronalysis, found: C,47.2; H,4.8; N,10.8%, $C_{10}H_{12}N_2SO_4$ requires: C,46.9; H,4.7; N,10.9%; NMR: ($d_6$-DMSO): 1.2(3H,s), 2.5(1H,dd), 3.2(1H,dd), 4.1(1H,m), 6.2(2H,s), 6.5(1H,d), 7.0(1H,s), 7.4-7.5(3H,); obtained in 38% yield, starting from 1-acetyl-2-methyl-5-(nitromethylsulphonyl)indoline;

(Example 26): 4,6-dimethyl-5-(nitromethylsulphonyl)indoline, as a pale yellow solid, m.p 123° C.; microanalysis, found: C,48.8; H,5.3; N,10.3%; $C_{11}H_{14}N_2SO_4$ requires: C,49.0; H,5.2; N,10.3%; NMR: 2.4(3H,s), 2.5(3H,s), 3.0(2H,t), 3.5(2H,t), 4.2-4.4(1H, broad), 5.5(2H,s), 6.3(1H,s); obtained in 48% yield, starting from 1-acetyl-4,6-dimethyl-5-(nitromethylsulphonyl)indoline;

(Example 27): 2,4-dimethyl-5-(nitromethylsulphonyl)indoline, as a pale yellow solid, m.p. 118° C.; microanalysis, found: C,49.3; H,5.4; N,10.1%; $C_{11}H_{14}N_2SO_4$ requires: C,48.9; H,5.2; N,10.4%; NMR: 1.1(1H,d), 2.4(3H,s), 2.6(1H,dd), 3.2(1H,dd), 4.2(1H,m), 4.3-4.6(1H, broad), 5.5(2H,s), 6.4(1H,d), 7.7(1H,d); obtained in 55% yield, starting from 1-acetyl-2,4-dimethyl-5-(nitromethylsulphonyl)indoline;

(Example 28): 2,4,6-trimethyl-5-(nitromethylsulphonyl)indoline, as a pale yellow solid, m.p. 110° C.; microanalysis, found: C,50.8; H,5.7; N,9.6%; $C_{12}H_{16}N_2SO_4$ requires: C,50.7; H,5.6; N,9.85%; NMR: 1.3(3H,d); 2.4(3H,s); 2.5(3H,s); 2.55-2.7(1H,dd); 3.1-3.3(1H,dd); 4.0-4.3(1H,m); 5.5(2H,s), 6.3(1H,s), obtained in 55% yield, starting from 1-acetyl-2,4,6-trimethyl-5-(nitromethylsulphonyl)indoline.

EXAMPLE 29

Using a similar procedure to that described in Example 16, 1-acetyl-2,4,6-trimethyl-5-(nitromethylsulphonyl)indoline was obtained in 22% yield as a cream solid, m.p. 175° C.; microanalysis, found: C,51.7; H,5.3; N,8.5%; $C_{14}H_{18}N_2O_5S$ requires: C,51.5; H,5.6; N,8.6%; NMR ($d_6$-DMSO): 1.2(3H,d), 2.25(3H,s), 2.4(3H,s), 2.6(3H,s), 2.6-2.8(1H,d), 3.2-3.4(1H,dd), 4.6-4.8(1H,m), 6.4(2H,s), 7.7-8.0(1H,br). The original starting material 2,4,6-trimethylindole, was itself obtained as a yellow oily solid, NMR: 2.39(3H,s), 2.40(3H,s), 2.46(3H,s), 6.15(1H,s), 6.7(1H,s), 6.9(1H,s), 7.6(1H,br) using a similar procedure to that described in J. Org. Chem., 1981, 46(4), 781, starting from 2-bromo-1,1-diethoxypropane and 3,5-dimethylaniline. The intermediate 2,4,6-trimethylindoline was obtained by a similar procedure to that described in connection with 4,6-dimethylindoline in Example 17. It was converted to the corresponding 1-acetyl derivative, m.p. 75° C. without characterisation.

EXAMPLE 30

Using a similar procedure to that described in Example 16, 1-acetyl-2-methyl-5-(nitromethylsulphonyl)indoline, was obtained in 40% yield as an off-white solid, m.p. 276° C.; microanalysis, found: C,48.6; H,4.9; N,9.5%; $C_{12}H_{14}N_2SO_5$ requires: C,48.3; H,4.7; N,9.4%; NMR ($d_6$-DMSO): 1.3(3H,d), 2.3(3H,s), 2.8(1H,d), 3.5(1H,dd), 4.7(1H,m), 6.5(2H,s), 7.7-7.9(2H,m), 8.0-8.3(1H,6), starting from 1-acetyl-2-methylindoline.

EXAMPLE 31

The following illustrate representative pharmaceutical dosage forms containing a compound of the formula I, for example a compound exemplified hereinbefore, or a non-toxic salt thereof (hereafter referred to as "compound X"), for therapeutic or prophylactic use in humans:

| (a) Tablet I | mg/tablet |
|---|---|
| Compound X | 100 |
| Lactose Ph.Eur. | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound X | 50 |
| Lactose Ph.Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound X | 1.0 |
| Lactose Ph.Eur. | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | .10 |
| Lactose Ph.Eur. | 488.5 |
| Magnesium stearate | 1.5 |
| (e) Injection I | (50 mg/ml) |
| Compound X | 5.0% w/v |

| | | |
|---|---|---|
| 1 M Sodium hydroxide solution | 15.0% v/v | |
| 0.1 M Hydrochloric acid (to adjust pH to 7.6) | 4.5% w/v | |
| Polyethylene glycol 400 | | |
| Water for injection to 100% | | |
| (f) Injection II | (10 mg/ml) | |
| Compound X | 1.0% w/v | |
| Sodium phosphate BP | 3.6% w/v | |
| 0.1 M Sodium hydroxide solution | 15.0% v/v | |
| Water for injection to 100% | | |
| (g) Injection III | (1 mg/ml, buffered to pH 6) | |
| Compound X | 0.1% w/v | |
| Sodium phosphate BP | 2.26% w/v | |
| Citric acid | 0.38% w/v | |
| Polyethylene glycol 400 | 3.5% w/v | |
| Water for injection to 100% | | |

The above formulations may be obtained by conventional procedures well known in the pharmaceutical art. The tablets (a)–(c) may be enteric coated by conventional means, for example to provide a coating of cellulose acetate phthalate.

CHEMICAL FORMULAE

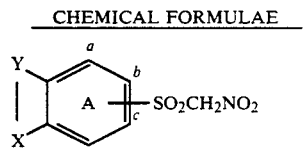  I

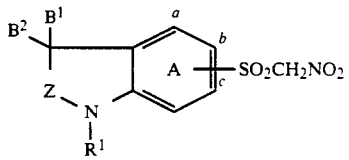  II

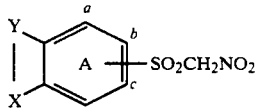  III

IVa

IVb

V

VI

CHEMICAL FORMULAE

VII

VIII

IX

XI

XII

XIII

[Note: Formula X is not used]

What is claimed is:
1. A nitromethane derivative of the formula I:

I wherein ring A may be unsubstituted or may bear one or more substituents independently selected from halogeno, (1–4C)alkyl and fluoro(1–4C)alkyl; X is an oxygen atom, or a group of the formula —S(O)$_n$— or —NR$^1$— in which n is zero or the integer 1 or 2, and R$^1$ is selected from the group consisting of hydrogen, (1–4C)alkyl, (1–6C)alkanoyl, benzoyl and phenyl(1–4C)alkyl, the benzene moiety of which last two groups may be unsubstituted or bear up to 3 substituents independently selected from the group consisting of halogeno, (1–4C)alkyl, (1–4C)alkoxy and fluoro(1–4C)alkyl; Y is a single linking group of the formula —(CH$_2$)$_m$—, —CH$_2$CH=CH—, —(CH$_2$)$_2$CH=CH— or —CH$_2$CH=CHCH$_2$—, in which m is the integer 2, 3 or 4 and a methylene (—CH$_2$—) group may be replaced by a carbonyl group, and which linking group may optionally bear up to four (1–4C)alkyl substituents and may be attached at either end to the group X; and wherein the group —SO$_2$CH$_2$NO$_2$ is located at position a, b or c in ring A; or a non-toxic salt thereof.

2. A compound as claimed in claim 1 wherein ring A may be unsubstituted or may bear one or more substituents independently selected from the group consisting of fluoro, chloro, bromo, iodo, methyl, ethyl, propyl, t-butyl, trifluoromethyl, pentafluoroethyl, 2,2,2-trifluoroethyl and 3,3,3-trifluoropropyl; X is oxygen, sulphur, sulphinyl, sulphonyl or a group of the formula —NR$^1$— in which R$^1$ is selected from the group consisting of hydrogen, methyl, ethyl, propyl, butyl, formyl, acetyl, propionyl, butyryl, phenylmethyl, 1-phenylethyl, 2-phenylethyl and 3-phenylpropyl, the benzene moiety of which last four groups may be unsubstituted or bear up to 3 substituents independently selected from the group consisting of fluoro, chloro, bromo, methyl, ethyl, methoxy, ethoxy and trifluoromethyl; and Y is a linking group selected from ethylene, trimethylene, tetramethylene and groups of the formula: —COCH$_2$—, —COCH$_2$CH$_2$—, —CH$_2$COCH$_2$—, —COCH$_2$CH$_2$CH$_2$—, —CH$_2$CH=CH— and —COCH=CH—, any of which linking groups may optionally bear up to four methyl, ethyl or propyl groups.

3. A compound according to claim 1 wherein the optional substituents on ring A are selected from the group consisting of fluoro, chloro, bromo, methyl, ethyl and trifluoromethyl; X is oxygen, sulphonyl or a group of the formula —NR$^1$— in which R$^1$ has any of the meanings defined in claim 1; and Y is a linking group selected from the group consisting of ethylene, trimethylene and groups of the formula: —CH$_2$CH$_2$C(CH$_3$)$_2$—, —CH$_2$CH$_2$CH$_2$C(CH$_3$)$_2$—, —CH$_2$C(CH$_3$)$_2$—, —COC(CH$_3$)=C(CH$_3$)—, COCH$_2$—, —COC(CH$_3$)$_2$—, —COCH$_2$C(CH$_3$)$_2$— and —CH=CHC(CH$_3$)$_2$—.

4. A compound according to claim 1 wherein ring A is unsubstituted or bears 1 or 2 methyl substituents; and X is oxygen, imino, N-acetylimino or N-ethylimino.

5. A pharmaceutical composition comprising a compound of the formula I, or a non-toxic salt thereof, as defined in claim 1, together with a pharmaceutically acceptable carrier or diluent.

6. A method of inhibiting the enzyme aldose reductase in a living animal requiring such inhibition which comprises adminstering to said animal an amount effective for inhibiting said enzyme of a compound of the formula I, or a non-toxic salt thereof, as defined in claim 1.

* * * * *